(12) United States Patent
Saad

(10) Patent No.: US 8,552,190 B1
(45) Date of Patent: Oct. 8, 2013

(54) TRISTHIOUREA TRIPODAL METAL COMPLEXES

(71) Applicant: Umm Al-Qura University, Makkah (SA)

(72) Inventor: Fawaz Saad, Makkah (SA)

(73) Assignee: Umm Al-Qura University, Makkah (SA)

( * ) Notice: Subject to any disclaimer, the term of this patent is extended or adjusted under 35 U.S.C. 154(b) by 0 days.

(21) Appl. No.: 13/769,233

(22) Filed: Feb. 15, 2013

(51) Int. Cl.
*C07F 15/06* (2006.01)
*C07D 401/14* (2006.01)

(52) U.S. Cl.
USPC ............................................ 546/2; 546/256

(58) Field of Classification Search
USPC .................................................. 546/2, 256
See application file for complete search history.

(56) References Cited

PUBLICATIONS

Wada, A. et al.: Steric and hydrogen-bonding effects on the stability of copper complexes with small molecules. Inorganic Chem., vol. 43, pp. 5725-5735, 2004.*
Tobey, S.L., "Energetics: The Fundamental Thermodynamic Parameters of Molecular Complexation via Electrostatic Interactions in Water", PhD Dissertation (May 2003), Chapter 2, pp. 55-108.

* cited by examiner

*Primary Examiner* — Charanjit Aulakh
(74) *Attorney, Agent, or Firm* — Richard C Litman

(57) ABSTRACT

The tristhiourea tripodal metal complexes are a group of coordination compounds having a transition metal linked by coordinate covalent bods to a chelating agent. The chelating agent has a tris-(6-amino-2-pyridylmethyl)amine (TAPA) backbone and three thiourea ligands bonded to the three legs of the TAPA backbone, respectively. The transition metal bonds to the amino groups of the TAPA backbone, and the thiourea ligands hydrogen bond to the anion guest remote from the transition metal. The chelating agent has a symmetrical $C_{3v}$ tripodal cavity that is selective for tetrahedral anions. The transition metal is selected from the group consisting of cadmium, manganese, cobalt, nickel, copper, and zinc. The tristhiourea tripodal metal complexes may be used in colorimetric sensors, selectively permeable membranes, filtration media for separating tetrahedral anions (such as phosphate and perchlorate) from mixtures, and similar applications.

8 Claims, 4 Drawing Sheets

といった.

TRISTHIOUREA TRIPODAL METAL COMPLEXES

BACKGROUND OF THE INVENTION

1. Field of the Invention

The present invention relates to coordination compounds, and particularly to tristhiourea tripodal metal complexes that include a transition metal bonded to a chelating agent having three thiourea ligands bridged by TAPA [tris(6-amino-2-pyridylmethyl)amine] that forms a tripodal cavity, making the compounds good anion receptors suitable for use in colorimetric sensors, selectively permeable membranes, filtration media for separations, etc.

2. Description of the Related Art

The use of molecular sensors is a unique method for the detection of species. Anions play an important role in a wide range of chemical and biological processes. Designing and synthesising anion receptors are of high importance in host-guest chemistry due to their significance in developing chemical sensors and membranes for selective transport and separation of anions. In particular, the synthesis of colorimetric anion sensors is of great importance because visual detection can offer qualitative and quantitative information. Efforts have been made to develop hydrogen-bonding donors (receptors) containing imine, amide, urea, thiourea, and also transition metal-based receptors. Urea and thiourea groups are powerful hydrogen bond donors, which have shown selective anion recognition through hydrogen bonding. $C_{3v}$ symmetrical systems seem to create a suitable cavity for anions, so long as those receptors have hydrogen bond donors able to bind the guest of interest.

Many important molecules, both organic and inorganic, contain tetrahedral anions, such as phosphate and perchlorate. An anion receptor having a cavity that is selective for tetrahedral anions and that takes advantage of the strong hydrogen bonding capabilities of thiourea is desirable. Thus, tristhiourea tripodal metal complexes solving the aforementioned problems are desired.

SUMMARY OF THE INVENTION

The tristhiourea tripodal metal complexes are a group of coordination compounds having a transition metal linked by coordinate covalent bods to a chelating agent having the general formula:

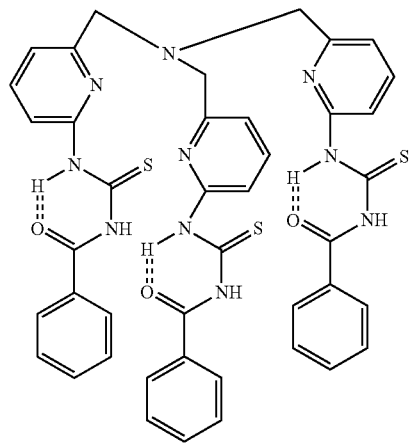

The chelating agent has a tris(6-amino-2-pyridylmethyl)amine (TAPA) backbone and three thiourea ligands bonded to the three legs of the TAPA backbone, respectively. The transition metal bonds to the amino groups of the TAPA backbone, and the thiourea ligands hydrogen bond to the anion guest remote from the transition metal. The chelating agent has a symmetrical $C_{3v}$ tripodal cavity that is selective for tetrahedral anions. The transition metal is selected from the group consisting of cadmium, manganese, cobalt, nickel, copper, and zinc. The tristhiourea tripodal metal complexes may be used in colorimetric sensors, selectively permeable membranes, filtration media for separating tetrahedral anions (such as phosphate and perchlorate) from mixtures, and similar applications.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The tristhiourea tripodal metal complexes are a group of coordination compounds having a transition metal linked by coordinate covalent bods to a chelating agent having the general formula:

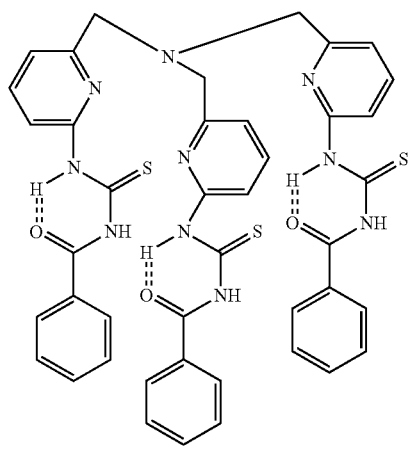

The chelating agent has a tris(6-amino-2-pyridylmethyl)amine (TAPA) backbone and three thiourea ligands bonded to the three legs of the TAPA backbone, respectively. The transition metal bonds to the amino groups of the TAPA backbone, and the thiourea ligands hydrogen bond to the anion guest remote from the transition metal. The chelating agent has a symmetrical $C_{3v}$ tripodal cavity that is selective for tetrahedral anions. The transition metal is selected from the group consisting of cadmium, manganese, cobalt, nickel, copper, and zinc. The tristhiourea tripodal metal complexes may be used in colorimetric sensors, selectively permeable membranes, filtration media for separating tetrahedral anions (such as phosphate and perchlorate) from mixtures, and similar applications.

Figure 1:
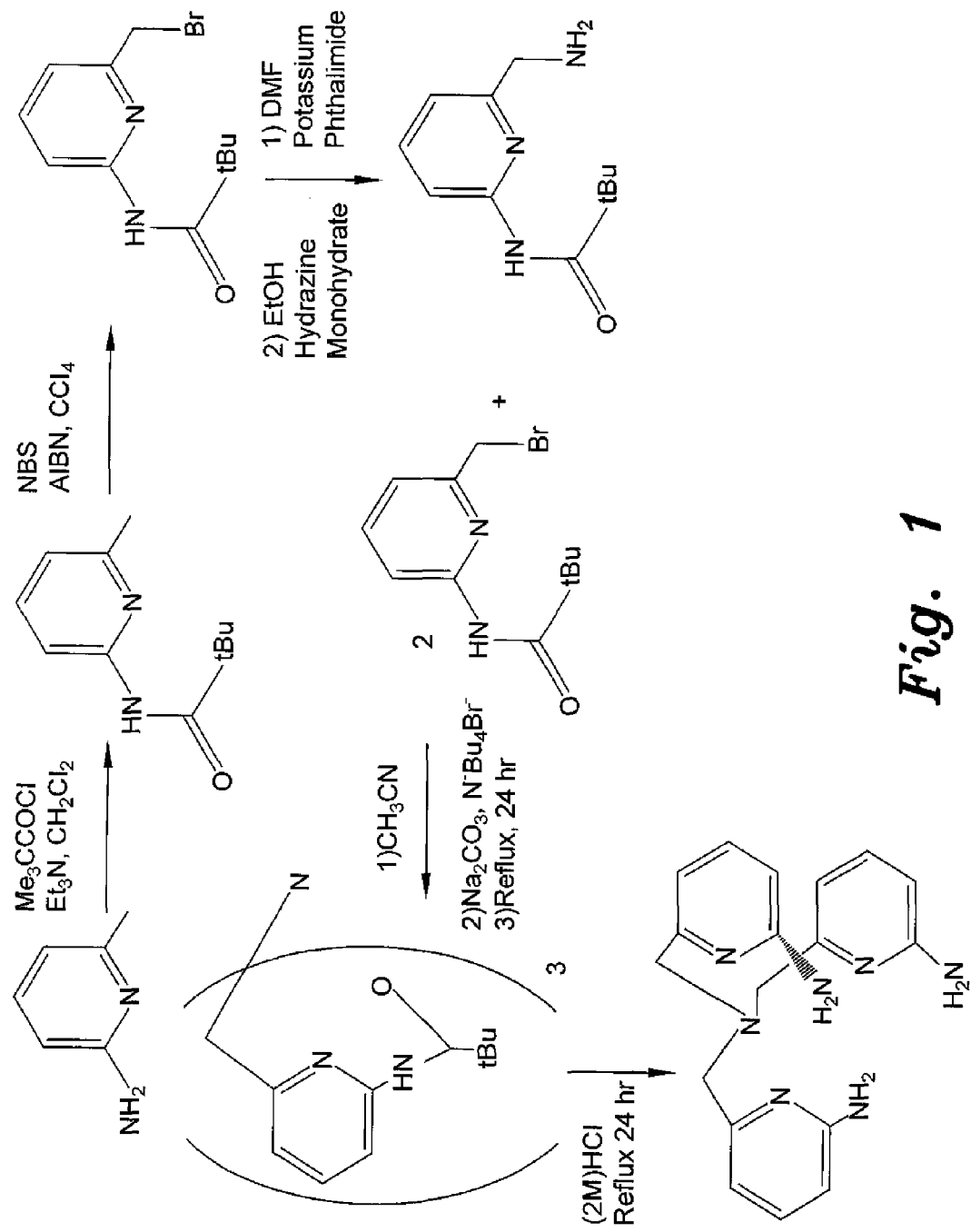
FIG. 1 is a diagram showing a reaction scheme for the synthesis of TAPA.

Tris(6-amino-2-pyridylmethyl)amine (TAPA), was prepared according to the reaction scheme shown in FIG. 1, as described more fully in M. Harata et al., *Chem. Lett.*, (1995), 61-62 and in K. Jitsukawa et al. *Inorg. Chim. Acta*, (2001), Vol. 324, 108-116

Figure 2:
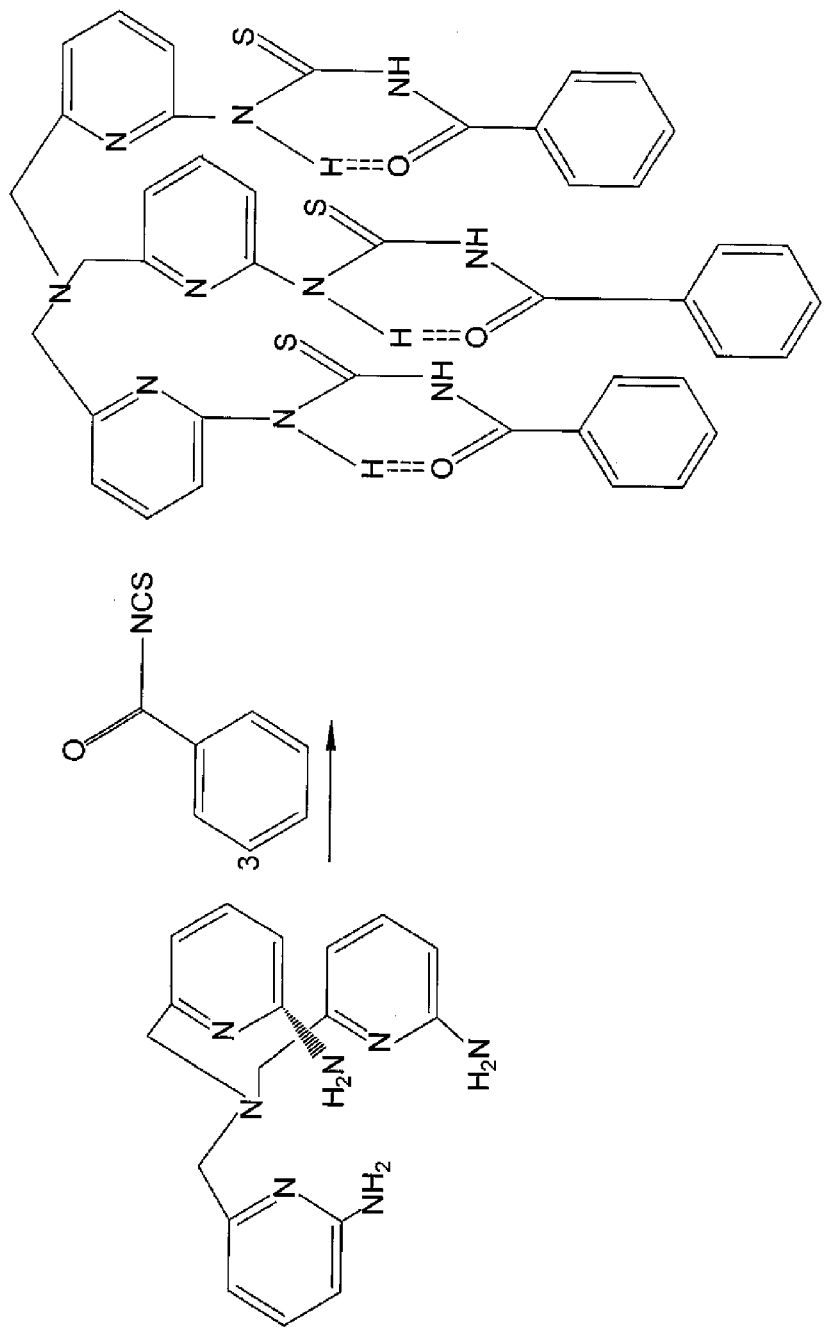
FIG. 2 is a diagram showing a reaction scheme for the synthesis of the chelating agent, which forms the tristhiourea tripodal metal complexes of the present invention when complexed with a transition metal.

The chelating agent (also referred to herein as $L^3$) was prepared according to the reaction scheme shown in FIG. 2. TAPA (3.40 g, 10.139 mmol) was dissolved in EtOH (200 mL of ethanol), and benzoyl isothiocyanate (4.9 mL, 30.4194 mmol) was added drop-wise. The mixture was heated to 40° C. for 30 minutes, and then allowed to cool to room temperature. The solvent was removed under reduced pressure. Ether was used to precipitate the product $L^3$ (the chelating agent) as a brown solid (3.147 g, 37% yield), having the empirical formula $C_{42}H_{36}N_{10}O_3S_3$. The product was evaluated by the following tests. $^1$H NMR showed δH (400 MHz; CDCl$_3$): 3.80 (6H, s); 7.39-7.43 (9H, m, Ar); 7.53 (3H, m, Ar); 7.69 (3H, t, Ar, J=7.8 Hz); 7.77 (6H, d, Ar, J=6.6 Hz); 8.61 (3H, d, Ar, J=4.1 Hz); 8.87 (3H, s, NH); 12.96 (3H, s, NH), and by $^{13}$C NMR showed δC (62.5 MHz; CDCl$_3$): δ9.6, 114.1, 120.8, 127.5, 129.1, 131.6, 133.6, 138.1, 150.3, 150.4, 166.2, 176.7. Mass spectroscopy showed ESMS (m/z): 825.2249 (100) $[L^3+H]^+$. [Calculated 825.2212]. Fourier Transform infrared spectroscopy showed IR KBr/cm$^+$: ν=3414 br, 3053 br, 1674 s, 1598 s, 1454 s, 1331 s, 755 s. Ultraviolet spectroscopy showed UV/Vis [λmax, nm (εM, M$^{-1}$cm$^{-1}$)] in THF: 268 (106,600), 288 (94,200) 310 (58,100).

By the foregoing reaction, the amino groups of the TAPA ligand were converted into thiourea groups via the drop-wise addition of 3 equivalents of benzoyl-isothiocyanate in ethanol with continuous stirring and gentle heating up to 40° C. for 30 min. Following this addition, the reaction mixture changed from a clear yellow solution to a brownish suspension. After great effort using different solvents, such as acetone, CH$_3$CN, and CHCl$_3$, to try to isolate a clean product of $L^3$, it was found that diethyl ether was the best solvent for washing the brownish crude to isolate a white precipitate. $L^3$ is thought to be much more interesting than bisthiourea ligands in terms of binding small oxyanions due to the $C_{3v}$ symmetrical structure of the chelating agent. The extra H-bonding arm may make this ligand more efficient for binding tetrahedral anions. The binding of an anion may be supported by the presence of three intramolecular hydrogen bonds occurring between the C=O bond of the benzoyl and the N—H bond of thiourea, and that will make the other NH bond point towards the cavity. Prior art ligands that have a TPA backbone and guanidimium legs that form a tripodal cavity can accommodate an anion that may also be binding to the metal center, but the present metal complexes will have the anion more remote to the metal center.

The chelating agent (1 equivalent, typically 0.077 mmol) was dissolved in the minimum amount of CHCl$_3$ in the case of cadmium, or THF for all other compounds (typically 3 mL). The solutions were warmed to about 60° C. to ensure that the chelating agent fully dissolved. To this stirring solution, the metal perchlorate salt (1 equivalent) dissolved in acetonitrile (ca. 2 mL) was added dropwise and left stirring for 2-3 hours with no precipitation occurring. A color change was observed for Mn$^{2+}$ (yellow) and Ni$^{2+}$ (green). However, a colorless solution was obtained for Zn$^{2+}$ and Cd$^{2+}$. Recrystallization of the compounds typically involved the diffusion of diethyl ether into a mixture of acetonitrile and THF or CHCl$_3$ solutions, which were first filtered through Celite. The yields from these reactions were moderate to high (24-69%). This crystalline material was then subsequently used for all spectroscopic measurements.

Example 1

A metal complex of the chelating agent with manganese was prepared as described above, and the product was analyzed by elemental analysis, mass spectroscopy, and infrared spectroscopy, with the following results. $[Mn^{II}(L^3)][ClO_4]_2\cdot CH_3CN$: colourless plate crystals (37% yield). Found: C, 47.36; H, 3.551; N, 13.86%. MnC$_{42}$H$_{36}$N$_{10}$O$_3$S$_3$(CH$_3$CN)(ClO$_4$)$_2$ requires C, 47.22; H, 3.51; N, 13.77%; ESMS m/z (%): 878.14 (100) $[Mn(L^3)-H]^+$; IR (KBr pellet, cm$^{-1}$): 3432(br), 1608(s), 1532(m), 1455(s), 1262(s), 1086(s), 706(s), 622(s).

Example 2

A metal complex of the chelating agent with cobalt was prepared as described above, and the product was analyzed by elemental analysis, mass spectroscopy, infrared spectroscopy, and ultraviolet spectroscopy, with the following results. $[Co^{II}(L^3)][ClO_4]_2$: dark red glassy solid (40% yield). ESMS m/z (%): 882.13 (60), $[Co(L^3)-H]^+$; IR (KBr pellet, cm$^{-1}$): 3419(br), 1613(s), 1539(m), 1447(m), 1263(s), 710(s), 1087(s), 626(s). UV/Vis [λ$_{max}$, nm (εM, M$^{-1}$cm$^{-1}$)] in CH$_3$CN: 260 (20500), 290 (14300), 310 (18000), 350 (6600), 500 (100), 630 (50), 960 (2).

Example 3

A metal complex of the chelating agent with nickel was prepared as described above, and the product was analyzed by elemental analysis, mass spectroscopy, infrared spectroscopy, and ultraviolet spectroscopy, with the following results. $[Ni^{II}(L^3)(CH_3CN)][ClO_4]_2\cdot 3.5\,(CH_3CN)\cdot 0.5\,(H_2O)$: green needle crystals (69% yield). Found: C, 48.12; H, 4.20; N, 15.99. NiC$_{51}$H$_{50.50}$N$_{14.50}$O$_{11.50}$Cl$_2$S$_3$ requires C, 48.05; H, 3.99; N, 15.94%; ESMS m/z (%): 881.14 (90), $[Ni(L^3)-H]^+$; IR (KBr pellet, cm$^{-1}$): 3464(br), 1616(s), 1539(m), 1488(s), 1261(s), 707(s), 1082(s), 622(s). UV/Vis [λ$_{max}$, nm (εM, M$^{-1}$cm$^{-1}$)] in CH$_3$CN: 260 (43950), 280 (36435), 320 (265000), 395 (2000), 560 (15), 795 (10), 850 (10), 1046 (16).

Example 4

A metal complex of the chelating agent with copper was prepared as described above, and the product was analyzed by elemental analysis, mass spectroscopy, infrared spectroscopy, and ultraviolet spectroscopy, with the following results. $[Cu^{II}(L^3)][ClO_4]_2$: green glassy solid (62% yield). ESMS m/z (%): 886.13 (100), $[Cu(L^3)-H]^+$; IR (KBr pellet, cm$^{-1}$): 3448(br), 1610(s), 1523(m), 1480(s), 1261(s), 709(s), 1088(s), 621(s). UV/Vis [λ$_{max}$, nm (εM, M$^{-1}$cm$^{-1}$)] in CH$_3$CN: 242 (35700), 262 (40825), 287 (31580), 311 (27535), 430 (900), 621 (60), 975 (10).

Example 5

A metal complex of the chelating agent with zinc was prepared as described above, and the product was analyzed by elemental analysis, mass spectroscopy, infrared spectroscopy, and $^1H$ and $^{13}C$ NMR, with the following results. [$Zn^{II}$ ($L^3$)][$ClO_4$]$_2$.$CH_3CN$.$CHC_3$: colourless needle crystals (24% yield). Found: C, 43.29; H, 3.17; N, 12.13%. $ZnC_{42}H_{36}N_{10}O_3S_3$ ($CHCl_3$)($CH_3CN$)($ClO_4$)$_2$ requires C, 43.37; H, 3.23; N, 12.37%; ESMS m/z (%): 887.14 (100) [$Zn(L^3)$-H]$^+$; $^1H$ NMR (400 MHz; $CD_3CN$): 4.41 (6H, s); 7.49 (6H, t, Ar, J=7.8 Hz); 7.59 (3H, d, Ar, J=7.8 Hz); 7.69 (6H, t, Ar, J=8.0 Hz); 7.78 (6H, d, Ar, J=7.5 Hz); 8.23 (3H, d, Ar, J=7.9 Hz); 10.23 (3H, s, NH); 13.39 (3H, s, NH). $^{13}C$ NMR (62.5 MHz; $CD_3CN$): 56.7, 123.2, 124.5, 129.5, 129.7, 131.7, 135.0, 144.5, 151.5, 155.0, 170.0, 180.7. IR (KBr pellet, cm$^{-1}$): 3437(br), 1623(s), 1522(s), 1447(s), 1261(s), 711(s), 1094(s), 622(s).

Example 6

A metal complex of the chelating agent with cadmium was prepared as described above, and the product was analyzed by elemental analysis, mass spectroscopy, infrared spectroscopy, and $^1H$ and $^{13}C$ NMR, with the following results. [$Cd^{II}$ ($L^3$)][$ClO_4$]$_2$.$0.5H_2O$: colourless plate crystals (7% yield). Found: C, 43.81; H, 3.17; N, 12.02%. $CdC_{42}H_{37}N_{10}O_{11.50}Cl_2S_3$ requires C, 44.04; H, 3.25; N, 12.22%; ESMS m/z (%): 937.12 (30), [$Cd(L^1)$-H]$^+$, 469.05 (20), [$Cd(L^1)/2$]$^+$; $^1H$ NMR (500 MHz; $CD_3CN$): 4.20 (6H, s); 7.38 (3H, d, Ar, J=7.5 Hz); 7.51 (3H, d, Ar, J=7.5 Hz); 7.57 (3H, t, Ar, J=7.6 Hz); 7.58 (3H, t, Ar, J=7.5 Hz); 7.76 (3H, t, Ar, J=7.5 Hz); 7.92 (3H, d, Ar, J=7.9 Hz); 7.94 (3H, d, Ar, J=7.9 Hz); 8.12 (3H, t, Ar, J=7.8 Hz) 10.27 (3H, s, NH); 13.60 (3H, s, NH). $^{13}C$ NMR (78 MHz; $CD_3CN$): 57.9, 122.3, 124.9, 129.6, 129.9, 131.9, 135.3, 143.3, 151.2, 154.0, 170.5, 181.1. IR (KBr pellet, cm$^{-1}$): 3450(br), 1601(s), 1522(s), 1451(s), 1263(s), 706(m), 1107(s), 620(s).

The infrared data observed for the metal complexes prepared in Examples 1-6 are very similar to those observed in bisthiourea. A very strong band at 1674 cm$^{-1}$, assigned to the $v(C=O)$ vibration of $L^3$ (Table 1), is shifted in all the metal complexes. A strong peak at 1331 cm$^{-1}$, assigned to the $v(C=S)$, is also typically shifted to lower energy between 1261-1263 cm$^{-1}$, indicating the coordination of the sulfur groups to metal centers, which reduces the bond order because of electrons donated by sulfur atoms to metals, and thus weakens the C=S bond. The shift of pyridine ring vibration at around 1550 cm$^{-1}$ and 1450 cm$^{-1}$ in all complexes indicates coordination from the pyridine ring nitrogens. All compounds reveal two characteristic unsplit infrared active bands at ~1,100 cm$^{-1}$ and ~622 cm$^{-1}$, indicative of ionic perchlorate ($T_d$ symmetry). All of these features are consistent with the X-ray diffraction data for the complexes.

Inspection of the $^1$H-NMR of the $Zn^{II}$ (Example 5) and $Cd^{II}$ (Example 6) metal complexes reveals that all protons are significantly deshielded, compared to the chelating agent. This effect is most likely caused by the presence of strong Lewis acidic $Zn^{II}$ cation.

The $^{13}C$ NMR spectra of the $Zn^{II}$ complex of Example 5 and the $^{13}C$ spectra of the cadmium metal complex of Example 6 shows that the upfield signal, in each case, is much weaker on comparison to the other signals. Such quaternary carbons signals are often weak due to slow relaxation. Both $^{13}C$ NMR spectra reveal all of the expected twelve carbon atoms.

The electronic spectra of the chelating agent and the metal complexes of $Co^{2+}$ (Example 2), $Ni^{2+}$ (Example 3) and $Cu^{2+}$ (Example 4) have been measured in solution, and the significant absorption bands are presented in Table 2. The electronic absorption spectra for the chelating agent ($L^3$) and all the above complexes show typical $\pi$-$\pi$* transitions at high energy (~265, ~285 and ~310 nm), which are characteristic of intraligand bipyridine $\pi$-$\pi$* transitions.

The Co(II) of Example 2 gives an MLCT band at 28,430 cm$^{-1}$. Although the crystal structure of the cobalt metal complex could not be obtained, but by assuming an octahedral geometry we may assign the spectrum. This $d^7$ complex has free ion states $^4F$, $^4P$, $^2P$, $^2D$, $^2G$, $^2H$, and $^2F$. In an octahedral electronic field, the lowest energy free ion state, $^4F$, splits into two orbital triplets, $^4T_{1g}$ and $^4T_{2g}$, and an orbital singlet, $^4A_{2g}$, while the next lowest energy free ion state is $^4P$, which remains unsplit ($^4T_{1g}$). Transitions from the ground state, $^4T_{1g}$ (F) to $^4T_{2g}$ (F), $^4A_{2g}$ (F) and $^4T_{1g}$ (P) lead to broad, banded absorptions in the visible and near infrared spectral regions. Typically, the spectrum of cobalt(II) in an octahedral environment consists of a broad band in the near infrared $^4T_{1g}$ (F)$\rightarrow$$^4T_{2g}$ (F), a broad and less intense band in the visible $^4T_{1g}$ (F)$\rightarrow$$^4A_{2g}$ (F), and another broad band in the visible $^4T_{1g}$ (F)$\rightarrow$$^4T_{1g}$ (P). The band at 10,390 cm$^{-1}$ is assigned to the $^4T_{1g}$ (F)$\rightarrow$$^4T_{2g}$ (F) transition, the broad absorption at 15,870 cm$^{-1}$ is assigned to $^4T_{1g}$ (F)$\rightarrow$$^4A_{2g}$ (F), and the band located at 19,980 cm$^{-1}$ is assigned as the $^4T_{1g}$ (F)$\rightarrow$$^4T_{1g}$ (P) transition.

The nickel compound of Example 3 gives an MLCT band at 25,200 cm$^{-1}$ and four d-d transitions at 9,560 cm$^{-1}$, 11,750 cm$^{-1}$, 12,575 cm$^{-1}$, and 17,850 cm$^{-1}$. These transitions could be ascribed to $^3A_{2g}\rightarrow$$^3T_{2g}$, $^3A_{2g}\rightarrow$$^3T_{1g}$ (F), $^3A_{2g}\rightarrow$$^1E_g$ (D) and $^3A_{2g}\rightarrow$$^3T_{1g}$ (P), respectively. Using these assignments yields $\Delta$=9,560 cm$^{-1}$; B=0.27.

TABLE 1

Electronic spectral assignments for $L^3$ and metal complexes

| Compound[a] | $\pi$-$\pi$* transitions/$\lambda$ (nm) | MLCT/$\lambda$ (nm) | d-d transitions/$\lambda$ (nm) | $\Delta^b$ cm$^{-1}$ | $B^b$ cm$^{-1}$ | $\beta$ |
|---|---|---|---|---|---|---|
| $L^3$ (Chelating agent) | 268(106600), 288(94200), 310(58100) | — | — | — | — | — |
| Example 2 (Cobalt) | 260(20500), 290(14300), 310(18000) | 350(6600) | 500(100), 630(50), 960(2) | — | — | — |
| Example 3 (Nickel) | 260(43950), 280(36435), 320(265000) | 395(2000), 560(15) | 795(10), 850(10) 1046(16) | 9560 | 285.4 | 0.27 |
| Example 4 (Copper) | 242(35700), 262(40825), 287(31580), 311(27535) | 430(900) | 621(60), 975(10) | — | — | — |

[a]Performed at room temperature (Examples 2, 3, 4) in $CH_3CN$ solution, $L^3$ in THF solution; numbers in parentheses indicate molar absorption coefficients $\epsilon$ ($M^{-1}cm^{-1}$).
[b]Values calculated by assuming an octahedral geometry.

The electronic spectrum of Cu(II), Example 4, gives an electronic spectrum of a MLCT at 23,250 cm$^{-1}$. The electronic spectra contain a very broad asymmetric peak in the visible region, which is very common for Jahn-Teller distorted $Cu^{II}$ complexes. For all ions with a $d^9$ configuration in an octahedral field, the lowest electron configuration is $t_{2g}^6$ $e_g^3$, leading to an $^2E_g$ term ground state and a $^2T_{2g}$ term excited state. Due to the asymmetric filling of the anti-bonding $e_g$ subset of ortibals, a tetragonal distortion arises in an attempt to remove the orbital degeneracy. Consequently, the $^2E_g$ term splits into $^2B_{1g}$ and $^2A_{1g}$, while the $^2T_{2g}$ term splits into $^2B_{2g}$ and $^2E_g$. Thus, three peaks should be observed. However, only two are observed for Example 4 (at 16,100 cm$^{-1}$ and 10,250 cm$^{-1}$), which are attributable to the transitions $v_1=$$^2B_{2g}\leftarrow$$^2B_{1g}$, $v_2=$$^2E_g\leftarrow$$^2B_{1g}$, in order of increasing energy. These transitions were tentatively labelled as ($d_{xy}\rightarrow d_{x^2-y^2}$) and ($d_{xz/yz}\rightarrow d_{x^2-y^2}$) respectively.

Alternatively, the compound may adapt a five coordinate trigonal bipyramidal structure similar to Example 3, which will not undergo a Jahn-Teller distortion, but will also give two peaks. Typically, trigonal bipyramidal $CuN_5$ complexes have a band envelope of 10,500-14,600 $cm^{-1}$, with a greater absorption intensity at lower energy. However, this is not seen with the metal complex of Example 4.

Cyclic voltammetry experiments were carried out. The cyclic voltammogram of the manganese compound, Example 1, reveals two irreversible reduction processes in the cathodic region, at −1.96 V and −1.30 V referenced against ferrocenium/ferrocene ($Fc^+/Fc$). Discrete mononuclear complexes of manganese in a heptacoordinated environment are quite rare. Thus, only limited comparisons can be drawn. The seven coordinate manganese (II) complex of Mn-TAPA exhibits the same wave processes at +1.2 V and +1.7 V (vs. SCE); 0.74 V and 1.24 V (vs. $Fc^+/Fc$). It seems difficult to ascribe unequivocally any of the waves to metal, rather than to ligand-centered electron transfer. Such a behavior of Mn (II) complexes is not uncommon. Interestingly, the voltammogram of the compound of Example 1 reveals no processes in the anodic region, and thus no indication of the Mn (II/III) redox couple, which is typically expected to be seen at about 0.34 V (vs. $Fc^+/Fc$).

The voltammogram of the $Co^{II}$ complex, Example 2, has quite similar electrochemical behaviour to the analogous $Mn^{II}$ complex of Example 1. It shows a similar irreversible reduction at −2.04 V (vs. Fc+/Fc). As with the $Mn^{II}$ compound of Example 1, without further investigation, or perhaps crystalline material, it is difficult to deduce the exact origins of this feature. However, the similarities of the voltammograms of the metal complexes of Examples 1 and 2 does suggest that the observed processes are largely ligand-based, The nickel complex, Example 3, consists of a series of small and ill-defined waves in the anodic as well as in the cathodic regions, suggesting rapid decomposition of the oxidized or reduced species formed. The overall picture does not change upon variation of the scan rate from 100 to 500 mV/s.

The voltammogram of the copper compound, Example 4, reveals a reversible redox process at −0.370 V, which is typical of $Cu^{II/I}$ species, with a peak-to-peak separation of 675 mV, most likely attributable to the $Cu^{II/I}$ redox couple. This couple is representative of a quasi-reversible behaviour.

X-ray crystallographic studies were performed on the manganese (Example 1), nickel (Example 3), zinc (Example 5), and cadmium (Example 6) compounds. The bond lengths and bond angles of the crystallographic studies confirm that the metal is connects to the bridge nitrogen, the three pyridyl nitrogens, and the three sulfur atoms of the thiourea ligand by coordinate bonds, whereas the perchlorate anion is bound by hydrogen bonds to the three thiourea ligands.

Figure 3:
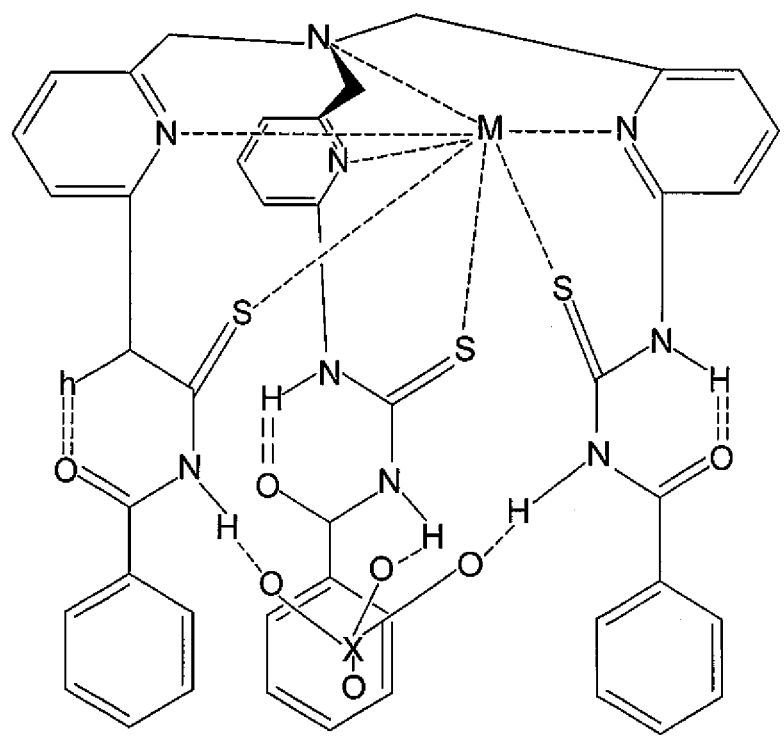
FIG. 3 is a diagram showing bonding of a tristhiourea metal complex according to the present invention to a tetrahedral anion, showing hydrogen bonding between the thiourea ligands and the anion.

In light of the test data, it is concluded that the tristhiourea tripodal metal complexes bond to tetrahedral complexes according to the bonding scheme shown in FIG. 3.

Example 7

Figure 4:
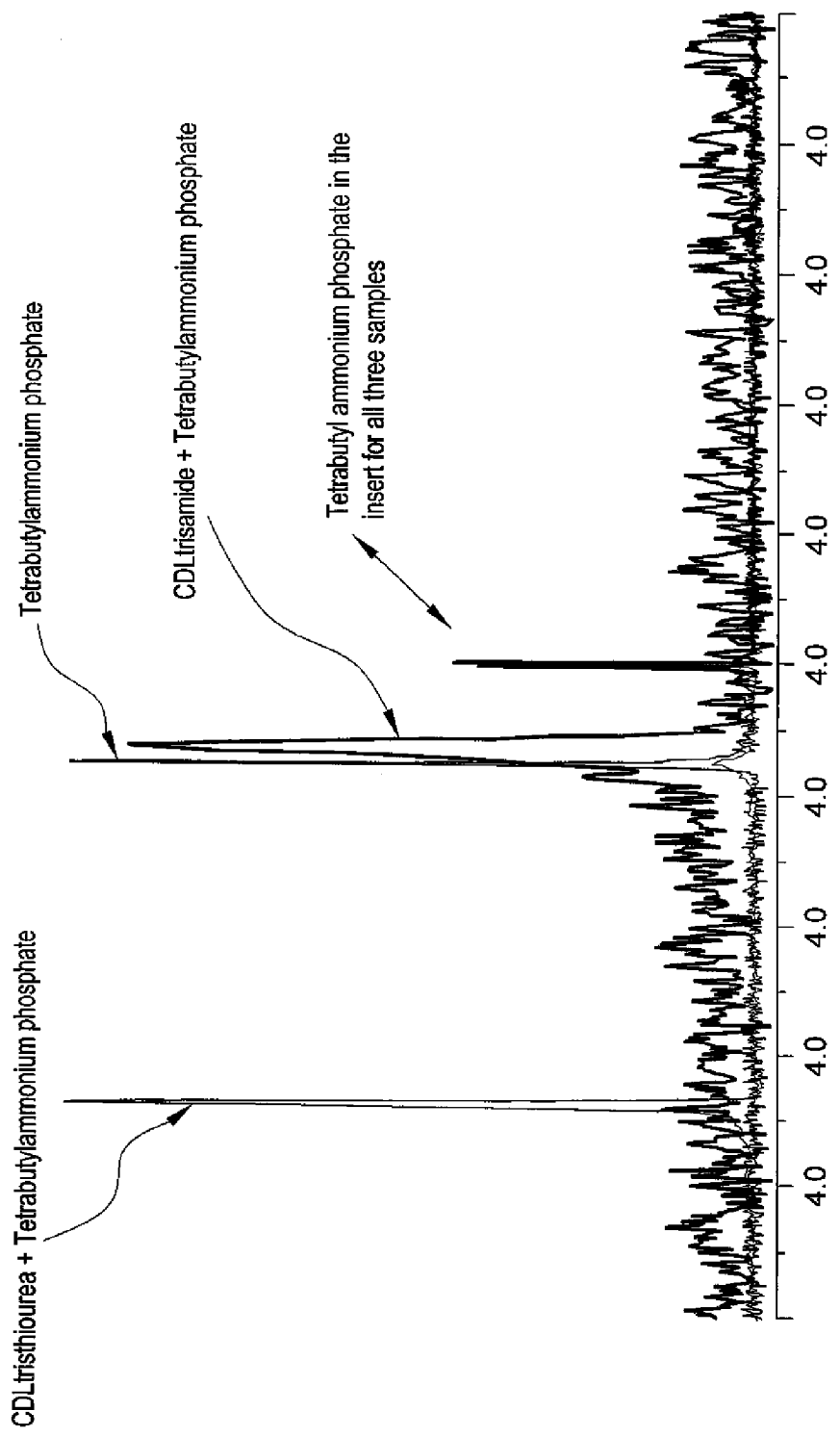
FIG. 4 shows comparative 31P-NMR spectra for complexes of tetrabutyl ammonium phosphate, $Cd^{II}$-TPPA with tetrabutylammonium phosphate and $Cd^{II}$-$L^3$ with tetrabutylammonium phosphate.

In an initial investigation to determine the ability of these complexes to bind the $H_2PO_4$ anion, we decided to utilise $^{31}$P-NMR spectroscopy. In theory, there is a possibility for the perchlorate ion that is in the cavity to be replaced with dihydrophosphate $H_2PO_4^-$. $^{31}$P-NMR is another way of proving whether the phosphate is bound or not. Practically, $^{31}$P-NMR was taken for three different samples of tetrabutyl ammonium phosphate, $Cd^{II}$-TPPA with tetrabutylammonium phosphate, and $Cd^{II}$-$L^3$ with tetrabutylammonium phosphate. All $^{31}$P-NMR were taken in the presence of insert, which consists of tetrabutylammonium phosphate in water. As shown in FIG. 4, a shift of 3.5 ppm is observed for the compound $Cd^{II}$-$L^3$ (Example 6) complexed with phosphate. This behaviour suggests a phosphate in $Cd^{II}$-$L^3$ being in different environment to the other two samples. No shift can be observed for the $Cd^{II}$ (TPPA) complex, which may be expected since there are three t-Butyl groups preventing phosphate from binding into the cavity. Efforts have been spent in an attempt to grow crystals of the phosphate species, but with no success. However, in this case, even with crystallographic data, it may be difficult to discriminate between $ClO_4^-$ and $H_2PO_4^-$.

It is to be understood that the present invention is not limited to the embodiments described above, but encompasses any and all embodiments within the scope of the following claims.

I claim:

1. A chelating agent for the formation of tristhiourea metal complexes having the formula:

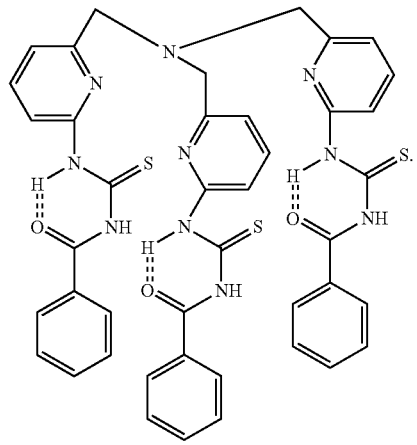

2. Tristhiourea tripodal metal complexes, comprising:
a chelating agent having the formula:

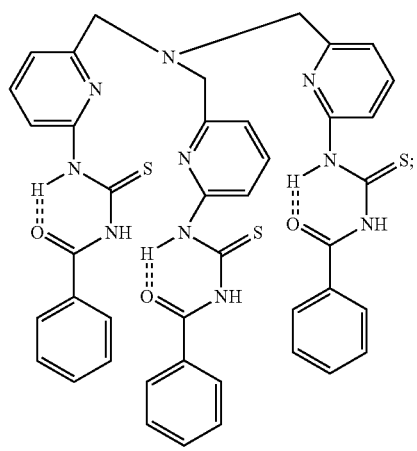

and
a transition metal bonded to the chelating agent, the transition metal being selected from the group consisting of manganese, cobalt, nickel, copper, zinc, and cadmium.

3. The tristhiourea tripodal metal complex according to claim 2, wherein the transition metal comprises manganese.

4. The tristhiourea tripodal metal complex according to claim 2, wherein the transition metal comprises cobalt.

5. The tristhiourea tripodal metal complex according to claim 2, wherein the transition metal comprises nickel.

6. The tristhiourea tripodal metal complex according to claim 2, wherein the transition metal comprises copper.

7. The tristhiourea tripodal metal complex according to claim 2, wherein the transition metal comprises zinc.

8. The tristhiourea tripodal metal complex according to claim 2, wherein the transition metal comprises cadmium.

* * * * *